United States Patent
Gavard Molliard et al.

(10) Patent No.: US 9,623,150 B2
(45) Date of Patent: *Apr. 18, 2017

(54) INJECTABLE HYDROGEL FOR THE LONG-TERM SUPPLEMENTATION OF GLYCEROL IN THE SKIN

(75) Inventors: Samuel Gavard Molliard, Bogeve (FR); Cyrille Vinchon, Chilly (FR)

(73) Assignee: ANTEIS S.A., Plan-les-Ouates (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/322,240

(22) PCT Filed: May 14, 2010

(86) PCT No.: PCT/FR2010/050937
§ 371 (c)(1),
(2), (4) Date: Jan. 19, 2012

(87) PCT Pub. No.: WO2010/136694
PCT Pub. Date: Dec. 2, 2010

(65) Prior Publication Data
US 2012/0108674 A1   May 3, 2012

(30) Foreign Application Priority Data
May 26, 2009   (FR) ..................... 09 53452

(51) Int. Cl.
*A61K 31/047* (2006.01)
*A61K 8/34* (2006.01)
*A61P 17/02* (2006.01)
*A61Q 19/08* (2006.01)
*A61L 27/52* (2006.01)
*A61K 8/04* (2006.01)
*A61K 8/73* (2006.01)
*A61L 27/20* (2006.01)

(52) U.S. Cl.
CPC .............. *A61L 27/52* (2013.01); *A61K 8/042* (2013.01); *A61K 8/735* (2013.01); *A61L 27/20* (2013.01); *A61Q 19/08* (2013.01); *A61K 2800/91* (2013.01); *A61L 2400/06* (2013.01)

(58) Field of Classification Search
CPC .......... A61K 8/042; A61K 8/735; A61Q 19/08
See application file for complete search history.

(56) References Cited

U.S. PATENT DOCUMENTS

| | | | |
|---|---|---|---|
| 5,095,037 A * | 3/1992 | Iwamitsu et al. .............. | 514/561 |
| 8,455,465 B2 * | 6/2013 | Gavard Molliard ............ | 514/62 |
| 2010/0184720 A1 | 7/2010 | Gavard Molliard et al. | |
| 2010/0316683 A1 | 12/2010 | Piron et al. | |

FOREIGN PATENT DOCUMENTS

| | | | |
|---|---|---|---|
| FR | 2 900 575 A1 | 11/2007 | |
| FR | 2 918 276 A1 | 1/2009 | |
| WO | 2008/068297 A1 | 6/2008 | |
| WO | WO/2009/024670 * | 2/2009 | ............... A61K 9/06 |

OTHER PUBLICATIONS

Definition of "prevention" from the Institute for International Medical Education [online], [Retrieved on Mar. 24, 2011]. Retrieved from the internet <http://www.iime.org/glossary.htm>. Published Feb. 2002, p. 1, 2, 26, 27 and 39.*
"Causes of Aging Skin" from AgingSkinNet [online], [Retrieved on Aug. 28, 2012]. Retrieved from the iinternet <http://www.skincarephysicians.com/agingskinnet/basicfacts.html>.*
The International Pharmacopoeia (1994), 3rd edition, vol. 4, p. 15-22.*
International Search Report, dated Jan. 24, 2011, from corresponding PCT application.

* cited by examiner

*Primary Examiner* — Layla Berry
(74) *Attorney, Agent, or Firm* — Young & Thompson

(57) ABSTRACT

An injectable hydrogel, includes, in weight, in a physiologically acceptable carrier fluid: 0.01 to 5% of glycerol and 0.1 to 5% of cross-linked hyaluronic acid, or one of the salts thereof; characterized in that the hyaluronic acid or one of the salts thereof is cross-linked by the formation of covalent bonds using bifunctional or polyfunctional molecules, the injectable hydrogel being sterilized in moist heat and having viscoelastic properties such that Tan δ at a frequency of 1 Hz is less than or equal to 1.10. A method for producing the hydrogel, to a kit containing the hydrogel, as well as to the use thereof in dermatology are also described.

16 Claims, 1 Drawing Sheet

INJECTABLE HYDROGEL FOR THE LONG-TERM SUPPLEMENTATION OF GLYCEROL IN THE SKIN

FIELD OF THE INVENTION

The present invention relates to an injectable hydrogel for the long-term supplementation of glycerol in the skin.

The present invention also relates to the method and to the use of the aforementioned hydrogel in the area of dermatology.

BACKGROUND OF THE INVENTION

Glycerol, an endogenous molecule, is a trihydroxy alcohol that has a key role in the skin. Endogenous glycerol notably plays a major role in hydration of the skin, in skin elasticity and in repair of the epidermal barrier (*British Journal of Dermatology*, 159(1):23-34, July 2008, Fluhr, J. W.; Darlenski, R. *; Surber).

The various beneficial effects of glycerol on the epidermis notably include hydration of the stratum corneum (the outermost layer of the skin), the barrier function of the skin, the mechanical properties of the skin, protection against irritant stimuli and acceleration of the process of wound healing (*British Journal of Dermatology*, 159(1):23-34, July 2008, Fluhr, J. W.; Darlenski, R. *; Surber).

It is also known from the prior art that topical application of products containing glycerol improves the properties of the skin in diseases characterized by xerosis and by an epidermal barrier that has deteriorated, as is the case in atopic dermatitis.

Moreover, with age, we observe a decrease in the amount of glycerol in the skin.

It can be deduced from all of the foregoing that supplementation of glycerol is beneficial for the skin.

That is why many cosmetics have glycerol in their composition. Thus, with application once or twice a day, the skin benefits from the positive effects of glycerol. However, this solution requires topical treatment of the skin every day.

Just like the use of a cosmetic, injection of an aqueous solution of glycerol in the skin makes it possible to benefit from the positive effects of glycerol in the very short term. In fact, almost all of the glycerol injected migrates rapidly from the zone of injection to the stratum corneum, and then is removed from the surface of the skin by daily washing. Thus, the beneficial action of glycerol is "one-off" (*PNAS*, 100(12):7360-7365, June 2003, Hara, M. W.; Verkman, A. S./*Journal d'Investigation Dermatologique*, 125: 288-293, 2005, Choi, H. C).

Injectable solutions of glycerol containing hyaluronic acid (HA) are described in the prior art. Owing to their viscoelastic characteristics, these solutions appear to allow delayed release of glycerol. However, when injected into the skin, these solutions do not provide long-term supplementation of glycerol (supplementation for a period of at most one week). In fact, hyaluronic acid is metabolized within the skin in less than a week (*Wenner-Gren International series; The chemistry, biology and medical applications of hyaluronan and its derivatives*, Laurent, T. C.).

Consequently, an injectable hydrogel providing gradual, long-term release of glycerol in the skin does not exist in the prior art.

SUMMARY OF THE INVENTION

Thus, the aim of the invention is to propose a novel injectable hydrogel that has numerous qualities and which avoids some of the drawbacks mentioned above.

Accordingly, the invention relates to an injectable hydrogel comprising, by weight, in a physiologically acceptable carrier fluid: 0.01% to 5% of glycerol and 0.1% to 5% of a crosslinked biopolymer of hyaluronic acid or of one of the salts thereof, relative to the total weight of the hydrogel, characterized in that hyaluronic acid or one of the salts thereof is crosslinked by formation of covalent bonds between the chains of said biopolymer by means of bifunctional or polyfunctional molecules, said injectable hydrogel being sterilized in moist heat and having a Tan δ at a frequency of 1 Hz less than or equal to 1.10.

The parameter Tan δ is a usual rheological parameter, which is defined as the tangent of the phase angle, said phase angle being the phase difference between stress and strain during an oscillatory rheological test. The tangent of the phase angle makes it possible to characterize the viscoelastic properties of a gel, notably based on crosslinked hyaluronic acid as was demonstrated in the work by Falcone (*Journal of Biomedical Material Research*, part A, January 2008, Falcone, S. J.; Berg, R. A.). For a gel based on crosslinked hyaluronic acid, the parameter Tan δ is probably correlated with the persistence of the gel in the skin, i.e. its presence at the injection site.

Completely surprisingly, a hydrogel based on 0.01% to 5% of glycerol and 0.1% to 5% of hyaluronic acid crosslinked by formation of covalent bonds, followed by sterilization in moist heat, said hydrogel possessing viscoelastic properties such that Tan δ at a frequency of 1 Hz is less than or equal to 1.10, makes it possible:

- to increase considerably the duration of release of glycerol in the skin relative to a gel based on glycerol and noncrosslinked hyaluronic acid sterilized in moist heat (type of gel with glycerol described in the prior art) (see comparative example 2);
- to increase significantly the duration of release of glycerol in the skin relative to a gel based on glycerol and crosslinked hyaluronic acid not sterilized in moist heat (see comparative example 1);
- to increase significantly the persistence, i.e. the presence of the gel at the injection site, relative to a gel based on glycerol and crosslinked hyaluronic acid not sterilized in moist heat (see comparative example 1).

This quadruple selection: covalent crosslinking of hyaluronic acid at a suitable concentration, presence of glycerol at a suitable concentration, sterilization in moist heat at a sufficiently high temperature and obtaining a gel possessing particular viscoelastic properties, makes it possible to obtain an injectable hydrogel with glycerol having a persistence of several months and a capacity for releasing glycerol in the skin over a long period. Thus, through the combination of the particular characteristics of the injectable hydrogel according to the invention, the glycerol is gradually eluted from the gel over a long period, thus allowing the skin to benefit from long-term supplementation of glycerol over time.

FIELD OF THE INVENTION

According to the invention, the concentration of glycerol is from 0.01% to 5 wt. %, preferably from 0.5% to 2.5% relative to the total weight of the hydrogel. Beyond 5 wt. %, the osmolarity of the hydrogel is too high, making it unsuitable for injection into the skin.

According to the invention, the concentration of crosslinked hyaluronic acid or of one of the salts thereof is from 0.1% to 5 wt. %, preferably from 0.5% to 3% relative to the total weight of the hydrogel.

According to the invention, the hydrogel possesses a Tan δ at a frequency of 1 Hz less than or equal to 1.10. Preferably, the hydrogel possesses a Tan δ at a frequency of 1 Hz less than or equal to 0.80.

Preferably, the molecular weight of the hyaluronic acid or of one of the salts thereof (before crosslinking) is between 1000 Da and $10\times10^6$ Da, preferably between 500,000 and $4\times10^6$ Da.

According to the invention, crosslinking is effected by means of bifunctional or polyfunctional molecules selected for example from epoxides, epihalohydrins and divinylsulfone, on noncrosslinked or already crosslinked hyaluronic acid with or without one or more other polysaccharides of natural origin. For example, the crosslinking agent used is butanediol diglycidyl ether (BDDE) or divinylsulfone (DVS).

According to a particular embodiment of the invention, the gel can also comprise other biocompatible polymers (such as polysaccharides of natural origin) and/or other pharmacologically active substances (such as lidocaine, a local anesthetic) or nonpharmacologically active substances (such as vitamins or mineral salts) having positive effects on the organism or on the hydrogel.

According to the invention, said injectable hydrogel is sterilized in moist heat.

Advantageously, sterilization is carried out at a temperature above 100° C. Preferably, sterilization is carried out at a temperature above or equal to 121° C.

For example, one of the following sterilization cycles can be used: 131° C. for 1 min/130° C. for 3 min/125° C. for 7 min/121° C. for 20 min or 121° C. for 10 min.

The present invention also relates to a process for manufacturing an injectable hydrogel as described above, comprising the steps consisting of:
a) preparing a first mixture comprising at least 0.1% to 5 wt. % of a crosslinked biopolymer of hyaluronic acid or of one of the salts thereof by formation of covalent bonds between the chains of said biopolymer by means of bifunctional or polyfunctional molecules,
b) adding 0.01% to 5 wt. % of glycerol before, during or after crosslinking of the biopolymer of hyaluronic acid or of one of the salts thereof during step a), so as to form a homogeneous mixture,
c) transforming the gel thus obtained into a form that is ready to use,
d) sterilizing the product in moist heat.

The glycerol can in fact be added to the gel based on crosslinked hyaluronic acid during manufacture of the gel based on crosslinked hyaluronic acid, i.e. at step a) before or during crosslinking of the gel based on hyaluronic acid or quite simply at the end of step a): after the crosslinking of the biopolymer.

During this process for manufacturing an injectable hydrogel, the sterilization temperature is above 100° C.

Preferably, sterilization is carried out at a temperature above or equal to 121° C.

In particular, during the process for manufacture of the hydrogel, sterilization is carried out according to one of the following cycles: 131° C. for 1 min/130° C. for 3 min/125° C. for 7 min/121° C. for 20 min or 121° C. for 10 min.

The gel thus obtained possesses rheological characteristics such that Tan δ at a frequency of 1 Hz is less than or equal to 1.10 and is preferably less than or equal to 0.80.

One aim of the present invention also relates to a kit that is in the form of a syringe and contains the injectable hydrogel as described above.

According to one embodiment of the kit, this can be in the form of a vial or bottle containing the injectable hydrogel according to the invention and suitable for being taken up in an injecting syringe.

The present invention also relates to the use of an injectable hydrogel according to the invention or of the kit as described above, for improving the chemical, physical and mechanical characteristics of the skin of mammals.

In particular, the present invention also relates to the use of an aforementioned injectable hydrogel or of the kit as described above, for filling wrinkles and lines and/or for creating volume and/or for skin moisturization and/or for reviving epidermal cellular activity and/or for maintaining the mechanical properties of firmness and elasticity of the skin and/or maintaining epidermal and dermal stimulation and/or for stimulating the antioxidant activity of the dermis and/or preventing skin aging and/or accelerating the process of wound healing.

BRIEF DESCRIPTION OF THE DRAWINGS

The invention will be better understood and other aims, details, characteristics and advantages thereof will become clearer on reading the following description of examples of carrying out the invention, referring to the appended figures in which.

similarly.

EXAMPLE OF CARRYING OUT THE INVENTION

Figure 1:
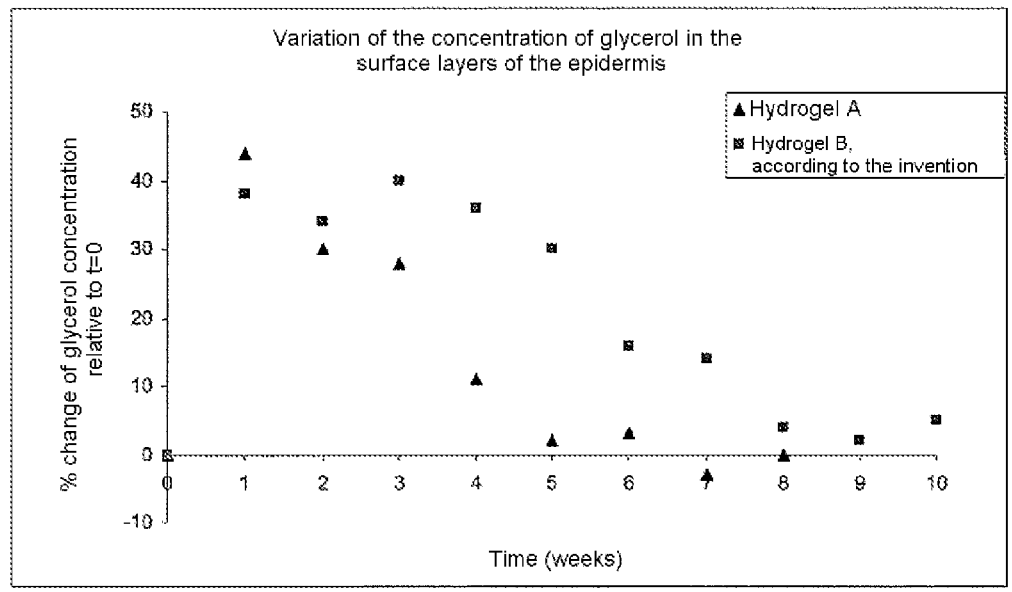
FIG. 1 presents a curve showing the percentage change in the concentration of glycerol in the surface layers of the epidermis from two gels: gel A (gel that has not undergone sterilization in moist heat) and gel B (according to the invention) over time in weeks.

An example of preparation of a hydrogel is presented for illustrating the invention, but it does not in any way limit the scope of the invention.

3.5 g of sodium hyaluronate (MW=$2.2\times10^6$ Da) is added to 25 ml of a solution of NaOH at 1% (w/w). The mixture is left at rest for 1 h and then mixed with a spatula for 10 minutes. The crosslinking reaction is then started by adding 263 µl of butanediol diglycidyl ether (BDDE) and it is mixed with a spatula for 10 minutes. The reaction mixture is placed on a water bath at 50° C. for 2 h. The mixture is adjusted to physiological pH with 1M HCl. The volume is adjusted to 116 ml with a solution buffered at pH=7.

The gel thus obtained is then dialyzed for 24 h (regenerated cellulose, limit of separation: MW=60 kDa) against a solution buffered at pH=7 in order to remove residual crosslinking agent.

1.7% (w/w) of glycerol is added to the gel based on crosslinked hyaluronic acid, then the mixture is homogenized for 15 minutes using a spatula.

The gel is then put in 1 ml glass syringes.

The total concentration of sodium hyaluronate is measured at 2.1% (w/w).

The total concentration of glycerol is measured at 1.68% (w/w).

The pH of the gel is measured at 7.02 and its osmolarity at 308 mOsm/kg.

The measurement of initial biocontamination is less than 10 CFU/g.

Half of the syringes obtained constitute hydrogel A.

The other half of the syringes obtained are sterilized in moist heat following a cycle [131° C., 1 minute]. These syringes constitute hydrogel B, according to the invention.

The rheological properties of the hydrogels are investigated by means of a type AR1000 rheometer (TA instruments) with a flat geometry of 40 mm, an air gap of 1000 microns and an analysis temperature of 25° C.

For hydrogel A, the measured value of the viscoelastic parameter Tan δ (at 1 Hz) is equal to 0.51.

For hydrogel B, the measured value of the viscoelastic parameter Tan δ (at 1 Hz) is equal to 0.67.

Comparative Test 1 Between Hydrogel A And Hydrogel B (According to the Invention) from the Above Example:

Tests In Vivo on Rabbit:

Four calibrated intradermal injections of 0.2 ml of hydrogel A and four calibrated intradermal injections of 0.2 ml of hydrogel B (hydrogel according to the invention) were performed on one and the same rabbit.

At t=0, the presence of a "papule" is found at each injection site, proof of the presence of the gel at the injection site. The diameter of each papule is measured with a caliper gauge and then the initial average area of one papule is calculated for hydrogel A and for hydrogel B.

At t=3 months, the presence of all of these papules is still found for the 2 types of hydrogels injected (the papules have an average area greater than ½ the initial average area of the 4 papules of hydrogel A or of the 4 papules of hydrogel B).

At t=6 months, it is found that the papules formed with hydrogel B according to the invention are still present (the papules have an average area greater than ½ the initial average area of the 4 papules of hydrogel B) whereas the papules obtained with hydrogel A are now barely visible (the papules have an average area less than ½ the initial average area of the 4 papules of hydrogel A).

Hydrogel B according to the invention therefore possesses a persistence that is significantly greater than that of hydrogel A.

In addition, the concentration of glycerol in the surface layers of the epidermis of the rabbit, at each papule obtained, was measured once a week for a maximum of 10 weeks. The mean value of the glycerol concentrations determined is calculated for each gel investigated and for each time investigated. The variations of the glycerol concentration determined over time for hydrogel A and for hydrogel B are compared (see FIG. 1).

Faster kinetics of release of glycerol in the skin is found for hydrogel A than for hydrogel B according to the invention.

Comparative Test 2 between Hydrogel B (According to the Invention) from the Above Example and a Hydrogel Based on Noncrosslinked Hyaluronic Acid and Glycerol, Sterilized in Moist Heat (Hydrogel C Described Below):

A gel is constituted of 1.7% (w/w) of glycerol and 2.1% (w/w) of noncrosslinked hyaluronic acid (MW=2.2×10$^6$ Da) in a solution buffered at pH=7. After filling in 1 ml glass syringes, the gel is sterilized in moist heat following a cycle [131° C., 1 minute]. These syringes constitute hydrogel C.

The rheological properties of hydrogel C are investigated using a type AR1000 rheometer (TA instruments) with a flat geometry of 40 mm, an air gap of 1000 microns and an analysis temperature of 25° C.

For hydrogel C, the measured value of the viscoelastic parameter Tan δ (at 1 Hz) is equal to 0.64.

Tests In Vivo on Rabbit:

Four calibrated intradermal injections of 0.2 ml of hydrogel C were performed on the same rabbit as for the previous comparative test.

At t=0, the presence of a "papule" is found at each injection site, proof of the presence of the gel at the injection site. The diameter of each papule is measured with a caliper gauge and then the initial average area of one papule is calculated for hydrogel C.

At t=1 week, it is found that the papules obtained with hydrogel C are now barely visible (the papules have an average area of less than ½ the initial average area of the 4 papules of hydrogel C).

At t=2 weeks, it is found that all of the papules obtained with hydrogel C are no longer visible.

The hydrogel B according to the invention therefore possesses considerably greater persistence than hydrogel C.

Figure 2:
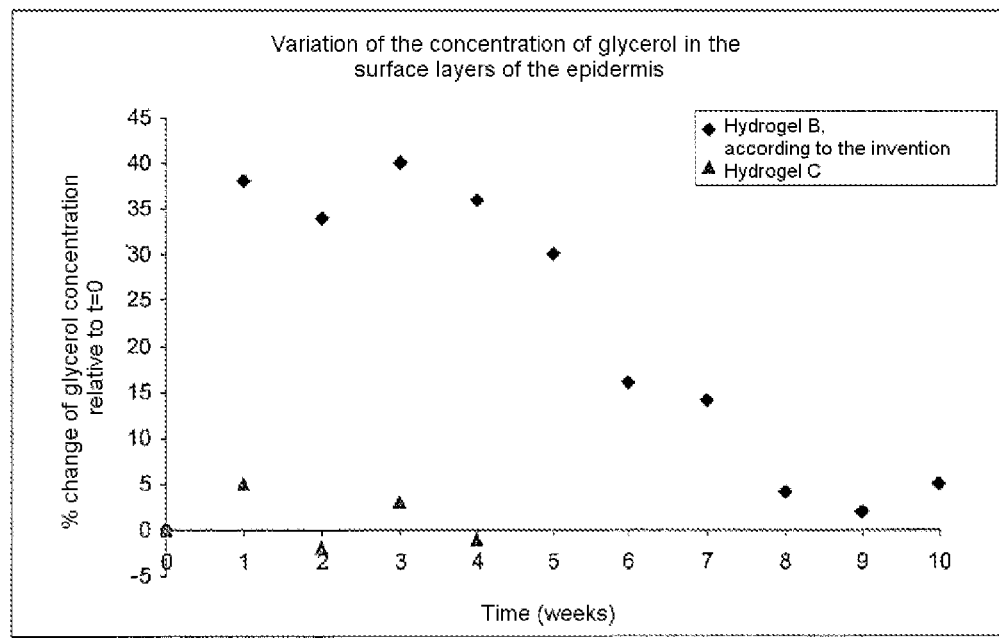
FIG. 2 presents a curve showing the percentage change in the concentration of glycerol in the surface layers of the epidermis from two gels: gel B (according to the invention) and gel C (gel based on noncrosslinked hyaluronic acid) over time in weeks.

In addition, the glycerol concentration in the surface layers of the epidermis of the rabbit, at each papule obtained, was measured after 1, 2, 3 and 4 weeks. The mean value of the glycerol concentrations determined is calculated for each time investigated. The variations of the glycerol concentration determined over time for hydrogel C and for hydrogel B are compared (see FIG. 2).

The kinetics of release of glycerol in the skin is found to be much faster for hydrogel C than for hydrogel B according to the invention.

Thus, real synergy is found between crosslinked hyaluronic acid and glycerol, after sterilization in moist heat in the formulation according to the invention. The presence of glycerol in the formulation according to the invention allows its persistence, i.e. the residence time of the gel at the injection site, to be increased significantly, and consequently it also makes it possible to increase the release of glycerol in the skin over time.

Thus, the gel based on glycerol and hyaluronic acid crosslinked by formation of covalent bonds, having undergone sterilization in moist heat and possessing viscoelastic properties such that Tan δ at a frequency of 1 Hz is less than or equal to 1.10, permits gradual, long-term release of glycerol in the skin. The glycerol and crosslinked hyaluronic acid act in synergy when they are combined according to the present invention. This can be explained by the fact that sterilization in moist heat, in the conditions of the invention, would permit thermal activation of the glycerol and/or of the crosslinked hyaluronic acid, which would permit better crosslinked HA-glycerol affinity, and consequently longer-term release of glycerol in the skin (relative to a gel not sterilized in moist heat).

It is important to point out, to clarify the relevance of the invention:

that a gel based on (non-crosslinked) hyaluronic acid with glycerol, sterilized in moist heat (type of gel described in the prior art), cannot ensure long-term release of glycerol in the skin its duration of release is in fact less than about 1 week;

that a gel based on hyaluronic acid crosslinked covalently with glycerol, not sterilized in moist heat, cannot give results equivalent to the formulation according to the invention (significantly shorter duration of release of glycerol in the skin);

that a gel based on hyaluronic acid crosslinked covalently with glycerol, possessing rheological properties such that Tan δ at a frequency of 1 Hz is greater than 1.10 does not possess suitable viscoelastic properties and/or sufficient persistence to obtain results equivalent to the formulation according to the invention. The duration of release of glycerol in the skin is in fact significantly shorter.

It is also important to point out that these elements could not be deduced by a person skilled in the art.

In fact, a person skilled in the art knows that crosslinking a gel based on hyaluronic acid makes it possible to increase the persistence of said gel in the skin. However, bearing in mind the low molecular weight of glycerol (MW=92 g/mol) and the low concentration of hyaluronic acid in the gel (concentration less than 5 wt. %), a person skilled in the art may easily assume that the glycerol molecule will easily migrate within the gel (steric hindrance of the gel induced by hyaluronic acid insufficient to trap the glycerol in the gel) and consequently that the glycerol will quickly be released in the skin. A person skilled in the art may also easily assume that crosslinking of hyaluronic acid will cause little change in the kinetics of release of glycerol in the skin relative to a gel based on noncrosslinked hyaluronic acid as bridging of the chains of hyaluronic acid does not produce a large increase of steric hindrance within the gel.

In other words, a person skilled in the art could not predict that the combination [glycerol+hyaluronic acid crosslinked by formation of covalent bonds+sterilization in moist heat+particular viscoelastic properties] would permit long-term, gradual release of glycerol in the skin.

Although the invention has been described in relation to particular embodiment, it is quite clear that it is by no means limited to this and that it comprises all the equivalent techniques of the means described as well as their combinations if the latter fall within the scope of the invention.

The invention claimed is:

1. An injectable hydrogel, for providing gradual long-term release of glycerol in the skin, comprising by weight relative to total weight of the hydrogel, in a physiologically acceptable carrier fluid:
   0.5% to 2.5% of glycerol, and
   0.5% to 3% of a crosslinked biopolymer of hyaluronic acid or a salt thereof,
   wherein the hyaluronic acid or salt thereof has a molecular weight of between $5 \times 10^5$ Da and $4 \times 10^6$ Da, and is crosslinked by formation of covalent bonds between chains of said biopolymer by butanediol diglycidyl ether (BDDE), said injectable hydrogel having been sterilized in moist heat and having a Tan δ at a frequency of 1 Hz less than or equal to 1.10,
   wherein the hydrogel is prepared by a process comprising:
   preparing a mixture comprising the crosslinked biopolymer of hyaluronic acid or salt thereof;
   adding glycerol to the mixture before, during or after crosslinking the biopolymer so as to form a homogeneous mixture;
   transforming the homogenous mixture into a gel; and
   sterilizing the gel in moist heat at a temperature of 130-131° C. for 1-3 min.

2. The injectable hydrogel according to claim 1, wherein the Tan δ at a frequency of 1 Hz is less than or equal to 0.80.

3. The injectable hydrogel according to claim 1, wherein the Tan δ at a frequency of 1 Hz is less than or equal to 0.67.

4. The injectable hydrogel according to claim 1, wherein the gel is sterilized in moist heat at a temperature of 131° C. for 1 min.

5. The injectable hydrogel according to claim 1, wherein the gel is sterilized in moist heat at a temperature of 130° C. for 3 min.

6. The injectable hydrogel according to claim 1, further comprising at least one additional biocompatible polymer, at least one pharmacologically active substance, and/or at least one nonpharmacologically active substance having positive effects on a mammalian organism or on the hydrogel.

7. The injectable hydrogel according to claim 1, applied for improving the chemical, physical and mechanical characteristics of the skin of mammals.

8. The injectable hydrogel according to claim 1, applied for filling wrinkles and lines, creating volume, skin moisturization, reviving epidermal cellular activity, maintaining firmness and elasticity of the skin, maintaining epidermal and dermal stimulation, stimulating antioxidant activity of the dermis, and/or accelerating wound healing.

9. A kit, comprising a syringe containing the injectable hydrogel according to claim 1.

10. A kit, comprising a vial or bottle containing the injectable hydrogel according to claim 1 and suitable to be taken up in an injecting syringe.

11. A process for manufacturing an injectable hydrogel, for providing gradual long-term release of glycerol in the skin, comprising:
   a) preparing a first mixture comprising at least 0.5 to 3 wt. % of a crosslinked biopolymer of hyaluronic acid or a salt thereof,
   wherein the hyaluronic acid or salt thereof has a molecular weight of between $5 \times 10^5$ Da and $4 \times 10^6$ Da, and is crosslinked by formation of covalent bonds between chains of said biopolymer by butanediol diglycidyl ether (BDDE),
   b) adding 0.5% to 2.5 wt. % of glycerol before, during or after the crosslinking of step a), so as to form a homogeneous mixture,
   c) transforming the mixture thus obtained into a gel, and
   d) sterilizing the gel in moist heat at a temperature of 130-131° C. for 1-3 min,
   wherein the sterilized gel has a Tan δ at a frequency of 1 Hz of less than or equal to 1.10.

12. The process according to claim 11, wherein the Tan δ at a frequency of 1 Hz is less than or equal to 0.80.

13. The process according to claim 11, wherein the Tan δ at a frequency of 1 Hz is less than or equal to 0.67.

14. The process according to claim 11, wherein the gel is sterilized in moist heat at a temperature of 131° C. for 1 min.

15. The process according to claim 11, wherein the gel is sterilized in moist heat at a temperature of 130° C. for 3 min.

16. A method of filling wrinkles and lines, creating volume, moisturizing skin, reviving epidermal cellular activity, maintaining firmness and elasticity of the skin, maintaining epidermal and dermal stimulation, stimulating antioxidant activity of the dermis, preventing skin aging, and/or accelerating wound healing in a subject, comprising intradermally injecting the subject with the hydrogel according to claim 1.

* * * * *